United States Patent [19]

Mehra

[11] Patent Number: 5,683,429
[45] Date of Patent: Nov. 4, 1997

[54] METHOD AND APPARATUS FOR CARDIAC PACING TO PREVENT ATRIAL FIBRILLATION

[75] Inventor: Rahul Mehra, Stillwater, Minn.

[73] Assignee: Medtronic, Inc., Minneapolis, Minn.

[21] Appl. No.: 640,046

[22] Filed: Apr. 30, 1996

[51] Int. Cl.⁶ .................................................. A61N 1/362
[52] U.S. Cl. ............................................................ 602/14
[58] Field of Search ........................................ 607/14, 15

[56] References Cited

U.S. PATENT DOCUMENTS

| | | |
|---|---|---|
| 3,937,226 | 2/1976 | Funke . |
| 4,088,140 | 5/1978 | Rockland . |
| 4,354,497 | 10/1982 | Kahn . |
| 4,821,723 | 4/1989 | Baker . |
| 4,872,459 | 10/1989 | Pless et al. ............... 607/15 |
| 4,971,070 | 11/1990 | Holleman . |
| 5,074,301 | 12/1991 | Gill . |
| 5,165,403 | 11/1992 | Mehra . |
| 5,193,536 | 3/1993 | Mehra . |
| 5,239,999 | 8/1993 | Imran . |
| 5,243,978 | 9/1993 | Duffin . |
| 5,292,338 | 3/1994 | Bardy . |
| 5,314,430 | 5/1994 | Bardy . |
| 5,314,448 | 5/1994 | Kroll . |
| 5,334,221 | 8/1994 | Bardy . |
| 5,366,485 | 11/1994 | Kroll . |
| 5,403,356 | 4/1995 | Hill . |
| 5,562,708 | 10/1996 | Combs et al. ............... 607/14 |

FOREIGN PATENT DOCUMENTS 9218198 of 0000 WIPO .

OTHER PUBLICATIONS

M. Allessie, M.D., et al. "Regional Control of Atrial Fibrillation by Rapid Pacing in Conscious Dogs", Circulation, vol. 84, No. 4, Oct. 1991, pp. 1689–1697.

C. Daubert et al., "Atrial Tachyarrhythmias Associated with High Degree Intratrial Conduction Block: Prevention by Permanent Atrial Resynchronization", European J.C.P.E. vol. 4, No. 1, 1994 pp. 35–44.

Primary Examiner—William E. Kamm
Attorney, Agent, or Firm—Reed A. Duthler; Harold R. Patton

[57] ABSTRACT

A method and apparatus for preventing fibrillation, particularly atrial fibrillation or flutter. In response to detection of an atrial premature beat at any given site in the atrial chamber, a low energy pulse burst is delivered to multiple sites of at least one chamber of the atrium for a time period sufficient to depolarize the entire atrium. Preferably, multiple pairs of sense electrodes are distributed about an atrial chamber or both atria to define discrete sensing sites and to widely distribute the simultaneously applied pacing energy pulse burst. Bradycardia pacing between the multiple electrode pairs is also preferably provided.

34 Claims, 6 Drawing Sheets

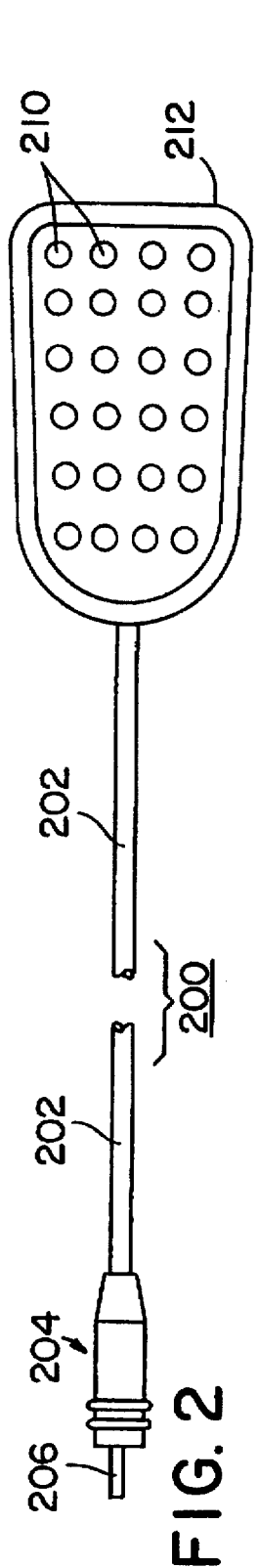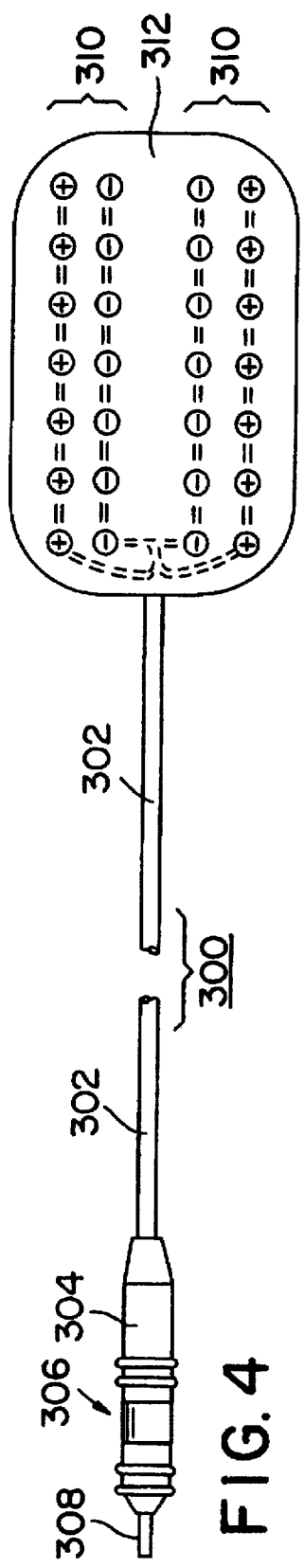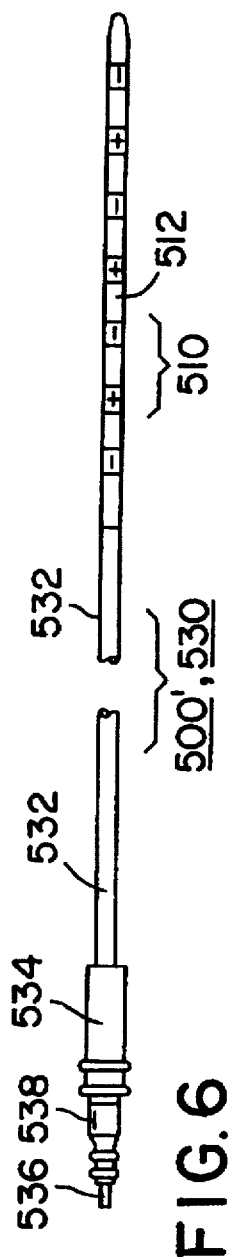

METHOD AND APPARATUS FOR CARDIAC PACING TO PREVENT ATRIAL FIBRILLATION

CROSS-REFERENCE TO RELATED APPLICATION

Reference is hereby made to commonly assigned, U.S. Pat. No. 5,562,708, issued Oct. 8, 1996, filed Apr. 21, 1994, for TREATMENT OF ATRIAL FIBRILLATION by Luc R. Mongeon et al., 08/495,251 filed Jun. 27, 1995, for DEFIBRILLATION THRESHOLD REDUCTION PACING SYSTEM by Xiaoyi Min et al., and 08/230,577 filed Apr. 21, 1994, for METHOD AND APPARATUS FOR TREATMENT OF ATRIAL FIBRILLATION by William J. Combs et al. all subject matter related to the present application.

FIELD OF THE INVENTION

The present invention generally relates to implantable stimulators and, more specifically, to implantable pacemakers, cardioverters and defibrillators and particularly to a burst pacing pulse stimulator for preventing the onset of atrial tachyarrythmias, e.g. atrial fibrillation.

BACKGROUND OF THE INVENTION

Atrial Fibrillation Considerations

Tachyarrythmias are episodes of high rate cardiac depolarizations, typically occurring in one chamber of the heart but which may be propagated from one chamber to the other, that are sufficiently high in rate and chaotic that cardiac output from the chamber(s) is compromised, leading to loss of consciousness and death, in the case of ventricular fibrillation, or weakness and dizziness, in the case of atrial fibrillation or flutter and non-sinus atrial and ventricular tachycardias. Atrial fibrillation and flutter is debilitating, due to the loss of atrial cardiac output contribution and interference with ventricular filling, but not life threatening unless it leads to ventricular fibrillation.

Defibrillation shock therapy drawbacks

Fibrillation has generally been treated by means of high energy cardioversion/defibrillation shocks or pulses, which, in the context of implantable anti-arrhythmia devices, are applied by means of large surface area electrodes, including an electrode on or in the chamber to be defibrillated. The high energy level is employed in order to simultaneously depolarize the bulk of the heart chamber to be defibrillated, which will include tissues in all stages of the depolarization-repolarization cycle at the time the pulse is delivered.

The battery life of an implantable stimulator depends on the amount of energy expended in delivering a therapy and the delivery frequency. The high energy level employed in order to defibrillate consumes considerable energy in the range of 1.0–30.0 Joules per delivered shock. Moreover, in the case of atrial fibrillation, the patient is not rendered unconscious if the ventricles continue to provide adequate cardiac output.

Unfortunately, the quantity of electrical energy required to cardiovert or defibrillate the atria is sufficient, in most cases, to cause a sudden, propagated pain in the patient's chest area or to stun the patient. Typically reported defibrillation thresholds between transvenous lead bearing electrodes placed to provide atrial cardioversion pathways between the right atrium (RA) and the coronary sinus (CS) or the superior vena cava (SVC) and the CS are 1.3±0.4 J. Significant discomfort and often intolerable pain is associated with transvenous shock therapy in this range, resulting in sedation of some patients and refusal to accept the therapy by other patients.

Moreover, there is concern that the attempt to defibrillate the atria will itself induce ventricular fibrillation leading to the death of the patient. In the hospital setting, the patient is carefully monitored, and induced ventricular fibrillation may be defibrillated. However, the clinical procedure still entails enough risk that drug therapies are preferred, and atrial defibrillation is used only after other therapies fail, leading to prolonged hospitalization or home care of the patient.

The same concern has deterred the development of implantable atrial defibrillators so that patients prone to bouts of atrial fibrillation or flutter could remain ambulatory. Despite considerable effort to develop an implantable system and method to terminate or prevent atrial fibrillation or flutter, none has yet been developed commercially. One possible approach that has been widely published is to combine the atrial and ventricular fibrillation detection and cardioversion/defibrillation capabilities in a single implantable system so that induced ventricular fibrillation could be terminated. However, such a system is quite complex and expensive, both in the hardware required and in the surgical procedure. Consequently, it remains a goal to provide a atrial cardioversion/defibrillation therapy that is unlikely to induce ventricular fibrillation and may be incorporated into an atrial chamber system only or that may be added to a ventricular chamber system for patient's prone to both atrial and ventricular arrhythmias.

Attempts to reduce atrial cardioversion energy

It was recognized early in the development of external ventricular defibrillators that a lower energy "synchronous cardioversion" shock could be employed to interrupt a ventricular tachycardia if the shock delivery was synchronized to a ventricular depolarization event, i.e. the R-wave. The term "cardioversion" generally includes such synchronous cardioversion and unsynchronized defibrillation.

In the context of atrial cardioversion, a proposed pacemaker/defibrillator is disclosed in PCT Publication No. WO 92/18198 by Adams et al. where the synchronization of the high voltage atrial cardioversion shock is to the R-wave in an effort to avoid inducing ventricular tachycardia or fibrillation. In either case, synchronization to an R-wave in a high rate, chaotic EGM has proven to be difficult to accomplish and not always effective to avoid inducing ventricular fibrillation.

Pacing preceding synchronized cardioversion

Faced with these difficulties, attempts have been made to first make the cardiac rhythm more regular so that the P-wave or R-wave may be detected and to then apply the synchronous cardioversion therapy. In commonly assigned U.S. Pat. No. 5,193,536 to Mehra, a pacemaker/cardioverter/defibrillator is described where the high atrial or ventricular rate is made more regular by delivering overdrive pacing pulses to capture the heart and by using the last overdrive pulse delivered as a synchronization event to time the delivery of the cardioversion shock. Another method is disclosed in U.S. Pat. No. 5,074,301 to Gill where a single pacing pulse is delivered to the atrium to allow the cardioversion shock to be delivered in the atrial refractory period. It is not suggested that the overdrive pacing pulses affect the cardioversion threshold.

In U.S. Pat. Nos. 5,314,448 and 5,366,485 to Kroll et al., a cardioverter/defibrillator is described having a set of cardioversion electrodes arranged around the patient's heart. When fibrillation is detected, the high output capacitors begin to be charged. As they are charged or after full charge is achieved, a "pretreatment" of the fibrillating heart muscle is commenced through the generation of a train of pulses from the voltage on the output capacitors and delivery of the pulses across the cardioversion electrodes. The capacitors are recharged and at the end of the recharge time period, the high energy cardioversion pulse is delivered across the cardioversion electrodes. It is stated that the pretreatment pulses begin the process of organizing the chaotically contracting myocardial cells and result in a reduction of cardioversion threshold and the total energy expended. It is emphasized that the pretreatment pulse voltages are well in excess of pacing level voltages and that the same cardioversion electrodes are employed to deliver the energy to the same myocardial cells as will be defibrillated by the cardioversion pulse. In this manner, the pretreatment pulses are delivered into the high current density regions of the current pathways in the heart chamber between the spaced apart cardioversion electrodes.

In the above-referenced '251 application, a method and apparatus for terminating fibrillation is disclosed using a burst of pacing energy, high frequency pulses applied into a low current density region of the cardiac tissue in the chamber in fibrillation prior to the delivery of one or more cardioversion energy pulses. The burst of pacing energy pulses is delivered between the pace/sense electrodes located in the low current density region of the cardioversion pathway around and through the heart chamber defined by the cardioversion energy distributed between the spaced apart cardioversion electrodes. The burst of pacing energy pulses injected into the low current density region results in the lowering of the cardioversion threshold, and the decreased energy cardioversion pulse effectively terminates the fibrillation episode. The burst of pacing energy pulses appears to develop a refractory island in the low energy region of the heart chamber that may itself lower the cardioversion energy, and also appears to prevent ectopic beats originating in the low energy region from refibrillating the heart.

Pacing to Interrupt a Detected Tachycardia

It was also recognized early in development of implantable pacemakers that certain tachycardias could be interrupted through the application of certain pacing therapies to the affected heart chamber. The pacing therapies include such pacing modalities as overdrive pacing, burst pacing, autodecremental overdrive pacing, and others, with or without synchronization to the intrinsic P-wave or R-wave. In one application, these pacing modalities were formulated to interrupt aberrant re-entrant conduction which may lead to sustained, "circus rhythm" tachycardias in one or more chambers of the heart. These approaches involved delivering timed single pacing energy pulses or bursts of pacing pulses each having sufficient energy to capture the heart to the same, single electrode pair used for sensing at a single site.

In this regard, it was also proposed that atrial and ventricular tachycardias could be interrupted and normal heart rate restored by the use of simultaneous or timed multi-site cardiac pacing. An early example of multi-site cardiac pacing to terminate ventricular tachyarrhythmias is disclosed in U.S. Pat. No. 3,937,226 issued to Funke. In this device, a number of small surface area pacing electrodes are provided to be applied to the ventricle, each coupled to a separate output circuit and amplifier. The disclosed device is equivalent to five or more separate cardiac pacemaker output circuits of conventional design, all adapted to be triggered to pace simultaneously at various locations around the ventricle. It is hypothesized that by stimulating simultaneously at locations spread around the ventricle, synchronously with a sensed QRS complex of a tachycardia episode, the tachycardia could be terminated by capturing the heart and producing a more nearly simultaneous depolarization of cardiac tissues. Improvements on the Funke concept to conserve energy or to distinguish high rate sinus depolarizations from ectopic depolarizations are set forth in U.S. Pat. No. 4,088,140 to Rockland et al., and in U.S. Pat. No. 4,354,497 to Kahn, respectively.

In a further U.S. Pat. No. 5,243,978 to Duffin, it is proposed that pacing pulses or bursts of pacing pulses may be delivered through the large surface area electrodes typically used for application of cardioversion/defibrillation shocks to the atrium or ventricle. The pacing pulses applied to these electrodes effect the simultaneous depolarization of tissue at multiple sites around the chamber being paced. Although no sensing algorithm is described, the proposed pacing therapy is stated to be in response to the detection of a tachyarrythmia, e.g. atrial or ventricular tachycardia.

Pacing pulses or pacing pulse bursts to terminate atrial fibrillation

Recently, the theoretical possibility of employing low energy pacing level pulses (i.e. less than 0.05 joules) to terminate atrial fibrillation has been explored. For example, in the recent article "Regional Control of Atrial Fibrillation by Rapid Pacing in Conscious Dogs", by Allessie et al, published in *Circulation*, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site, is reported. However, the depolarization wavefront created by such pulses does not propagate through the entire chamber due to the varying polarization states of the tissue surrounding the stimulation site. Consequently, it has not been demonstrated that this approach can defibrillate a heart chamber actually in fibrillation.

It is generally believed that the delivery of pacing pulse bursts to the atrium can induce atrial fibrillation, unless the delivery is synchronized to P-waves to assure that the pulse bursts occur within the refractory period of the atrium. This effect is discussed in U.S. Pat. No. 5,334,221 to Bardy which discloses a device which provides pulse bursts, synchronized to a P-wave, to the SA nodal fat pad in the atrium to reduce the sinus rate of patients who suffer from angina.

Despite this general belief, it has also been proposed to avoid synchronizing the delivered pacing pulse or burst to a detected depolarization to interrupt atrial fibrillation or flutter. In the above cited '577 application, the pacing pulses are simultaneously delivered at multiple sites distributed over a substantial portion of the atria or atrium to be treated. Rather than attempt to synchronize the delivered pulses to the high rate atrial electrogram sensed at a stimulation site, simultaneous pulse delivery at the multiple dispersed sites is intended to eventually result in capture of the atrial tissue at one or more of the stimulation sites. It is theorized that the propagation of the depolarization wavefront created in response to the delivered pacing pulse, toward cardiac tissue closely adjacent the site at which capture initially occurs, increases the probability that the adjacent tissue will be in an appropriate stage of the depolarization-repolarization cycle to be captured by the next pulse in the burst. As pulses of the burst continue to be delivered, therefore, the amount of atrial tissue captured should gradually increase, with the end result of capturing a sufficient amount of atrial tissue to terminate fibrillation.

Similarly, in the above cited '578 application, a series of low energy pulse bursts is delivered, separated by defined inter-burst intervals, and including bursts unsynchronized to atrial heart depolarizations. Detection of termination of atrial fibrillation during inter-burst intervals results in cancellation of further pulse bursts to prevent re-induction of fibrillation. The therapy is preferably delivered using multisite distributed electrode systems or large surface area electrodes about the atria or atrium.

Pacing to prevent atrial fibrillation or flutter

Atrial tachyarrythmias, including atrial tachycardia, flutter or fibrillation, may be preceded by one or more atrial premature beat (APB) spontaneously originating in an ectopic site in the atrium or triggered by a circus rhythm conduction from a preceding ventricular depolarization. Use of pacing energy pulses delivered at multiple atrial sites to prevent the occurrence of atrial tachyarrythmias including atrial flutter, which may in some cases progress to atrial fibrillation, (rather than interrupt such arrhythmias as described above) has also been investigated. For example, the article, "Atrial Tachyarrythmias Associated with High Degree Intratrial Conduction Block: Prevention by Permanent Atrial Resynchronization", by Daubert et al, *EUROPEAN J.C.P.E.*, Vol. 4, No. 1, 1994, pp. 35–44, discloses the delivery of pacing pulses to the right and left atria using a DDD pacemaker in a DAT mode with the atrial electrode at one atrial site and the ventricular electrode at another atrial site. If an atrial depolarization is sensed at the one atrial site, a closely timed single pace pulse is delivered to the other atrial site.

A further approach to preventing the onset of an atrial tachyarrythmia employing pacing energy pulses is proposed in U.S. Pat. No. 5,403,356 to Hill et al. employing multiple pairs of electrodes located in the triangle of Koch and/or an area of prolonged refractory period and, optionally, other areas of the atrium used in pacing and sensing combinations. If an atrial depolarization other than an APB is detected at any one pair of electrodes, synchronized pacing pulses are delivered to the other or all of the electrode pairs. The delivered pace pulses into the region of long refractory period is expected to make it less likely that an APB will trigger or degenerate into atrial fibrillation refractory. Thus, an APB is itself not responded to, and therefore, the reentry and re-triggering of successive APB's through a circus rhythm conduction pathway of the ventricular depolarization triggered by the preceding atrial depolarization or an ectopic ventricular depolarization is not avoided or treated.

The detection of atrial depolarizations and APBs is also complicated by the possibility that the far-field R-wave originating in the ventricle may be mistaken for a P-wave at the atrial sense amplifier.

Despite these advances, a need continues to exist for a system for preventing atrial fibrillation or flutter that is simple to implant, decreases energy consumption and pain perceived by the patient, and reliably distinguishes P-waves from far-field R-waves.

SUMMARY OF THE INVENTION

It is therefore an object of the present invention to provide a method and apparatus for preventing atrial fibrillation that may be otherwise triggered by an APB.

It is a further object of the invention to provide a pacing energy method and apparatus for avoiding the necessity of atrial cardioversion for atrial fibrillation and for thereby decreasing energy consumption of an implantable atrial cardioverter and pain perceived by the patient attendant to atrial cardioversion.

The present invention surprisingly accomplishes these objectives by applying prolonged low energy bursts of pulses to the atrium simultaneously at multiple sites upon detection of an APB in order to ensure that all sites are depolarized by the time that the burst terminates so that a circus rhythm is interrupted.

The simultaneous application of the low energy pulse bursts is effected either through epicardial patch leads implanted around the atria or by endocardial right atrial (RA) and coronary sinus (CS) leads or combinations of such leads. Each lead may have a single, large surface area electrode and lead conductor or multiple, discrete electrode surfaces of the same polarity or multiple, discrete electrode surfaces of the differing polarities forming closely spaced electrode pairs and lead conductors to each.

Preferably, normal bradycardia atrial pacing is also provided in the system wherein the single pacing stimulus is simultaneously applied across each of the pairs of electrodes in the particular system.

The burst of pacing energy pulses is prolonged sufficiently to depolarize all potential sites of origin of the APB so that they do not repeat and lead to atrial fibrillation.

It is envisioned that in most patients, the present invention will be practiced in conjunction with electrodes located in or on one atrial chamber. However, in some cases, electrodes may be applied to both atria.

While the invention is believed primarily beneficial in preventing atrial fibrillation in response to an APB, as a practical matter, it may be difficult to distinguish APBs that trigger atrial fibrillation from those that trigger atrial flutter, and atrial fibrillation and flutter may be simultaneously present in some patients. It is believed possible that the therapy may also be beneficial in preventing rhythms which physicians might identify as atrial flutter, without accompanying atrial fibrillation.

Unlike high voltage atrial defibrillation, the therapy provided by the present invention does not raise a corresponding risk of induction of ventricular tachyarrythmia because the pacing pulse burst energy level is low and confined to the atria.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIG. 2 is a plan view of an atrial epicardial electrode lead for providing multiple stimulation sites over the area of the epicardial patch that may be employed in the first lead system of FIG. 1;

FIG. 4 is a plan view of an atrial epicardial electrode lead for providing multiple discrete pairs of stimulation and sensing sites as employed in the second lead system of FIG. 3;

FIG. 6 is a plan view of a transvenous multi-polar lead which may be employed for atrial sensing and pacing in addition to or substitution for the leads illustrated in FIG. 5 for placement in the right atrium and/or the coronary sinus in relation to the left atrium;

DETAILED DESCRIPTION OF THE PREFERRED EMBODIMENTS

In commercial implementations, the invention may be embodied as part of an implantable pacemaker/cardioverter/defibrillator system, particularly an atrial and ventricular system of the type disclosed in commonly assigned U.S. Pat. No. 5,292,338 to Bardy. In such a system, large surface area cardioversion/defibrillation electrodes are present about the atria and the ventricles and may be employed for cardioversion or defibrillation in the event that less aggressive therapies fail to terminate the detected arrhythmia or it progresses to fibrillation.

However, the invention is preferably embodied as an atrial pacemaker only for use in patients who are not susceptible to ventricular fibrillation. The atrial electrodes in such case would be employed only for sensing P-waves and delivery of pacing pulses in a demand pacing mode in response to atrial bradycardia and delivery of burst pacing on detection of an APB. The delivery of the pacing pulses in the demand pacing mode is preferably simultaneously to all or a selected portion of all of the multiple electrode sites positioned around the atrium at the end of an atrial pace escape interval. The timed delivery of pacing energy pulse bursts may be to all multiple electrode sites positioned around the atrium in response to a single APB detected at any of the multiple electrode sites by a sense amplifier coupled to the electrode site where the depolarization wave is first detected.

Figure 1:
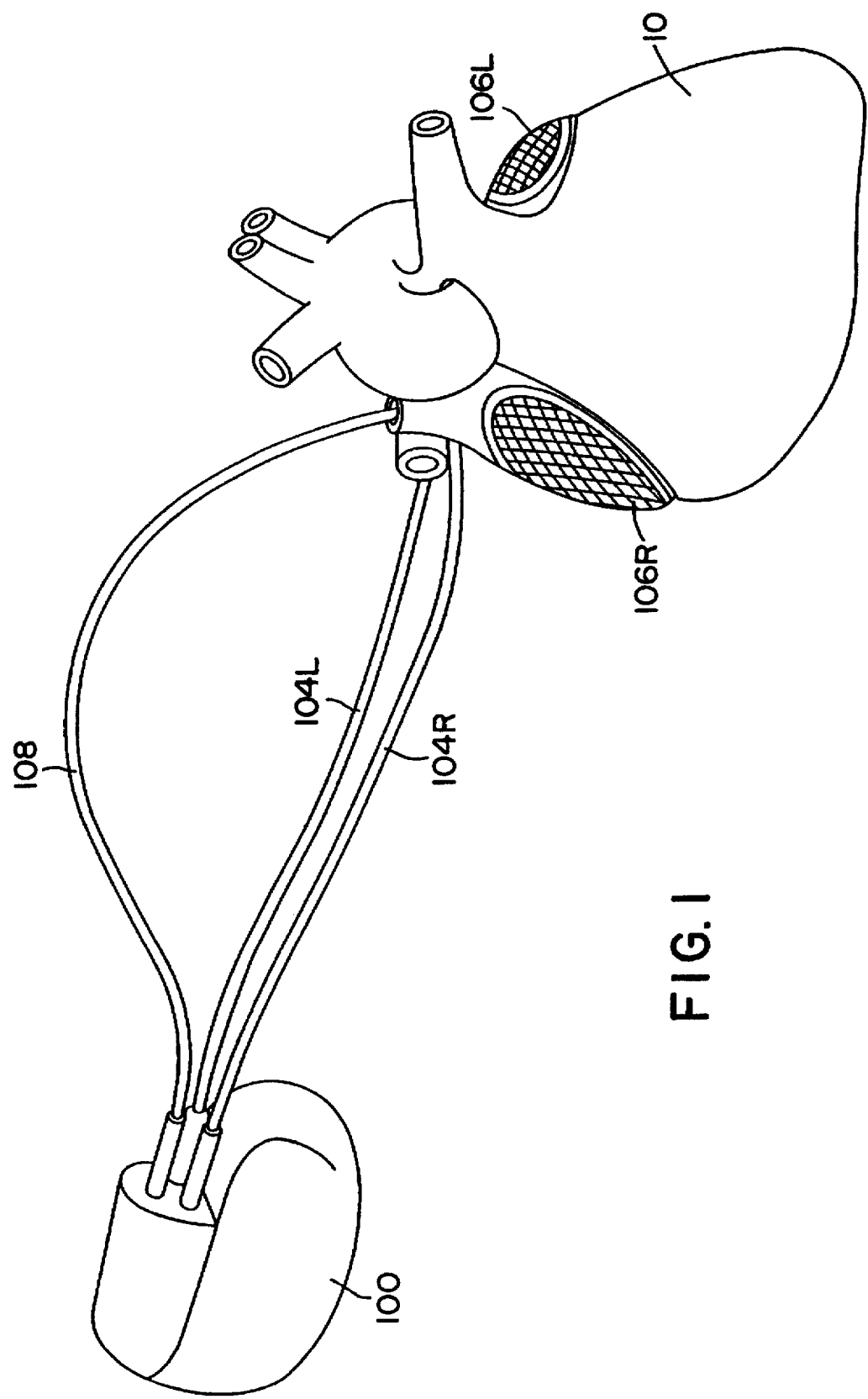
FIG. 1 is a plan view of a pacemaker implantable pulse generator (IPG) and a first associated lead system of the type in which the present invention may be embodied, illustrating the location of the leads and electrodes in relation to the atria of a human heart.

FIG. 1 is a plan view of a first embodiment of such an implantable pulse generator (IPG) 100 and an associated lead system in conjunction with a human heart 10. As illustrated, the lead system includes a conventional endocardial RA pace/sense electrode bearing lead 102, and two epicardial patch electrode leads 104R and 104L. Leads 104R and 104L are provided with large surface area electrodes 106R and 106L, respectively, adapted to located epicardially on the right and left atria. Optionally, the system may also include a transvenous RA lead.

The illustrated patch electrodes 106R and 106L are adapted from the disclosure of U.S. Pat. No. 4,821,723 issued to Baker, et al., reduced in size to allow location on the right and left atria. However, it is believed that any pair of large surface area defibrillation electrodes appropriately sized for location in contact with only on the atria, and preferably extending over a majority of the accessible atrial tissue, may be usefully employed to practice the present invention. For example, exposed coil electrodes as disclosed in U.S. Pat. No. 4,971,070 issued to Holleman, et al., incorporated herein by reference in its entirety, may also be used. Electrodes of this type have in fact been tested, and it has been determined that, in conjunction with a cardiac pacemaker output stage modified to pace into a 50 ohm load, reliable cardiac pacing may be accomplished with an output of 10–15 volts. In any case, it is desired that the epicardial electrodes 106R and 106L have a relatively large surface area and be dispersed over a substantial portion of the atrial epicardium in order to simultaneously effectively apply the burst pacing to an effective multitude of electrode sites.

In a variation, one or more epicardial leads may be combined with one or more endocardial lead 108, e.g. a RA or a CS endocardial lead. The RA or CS lead 108, if present, may be a conventional bipolar pace/sense lead, serving in parallel to perform additional sensing sites and pacing energy distribution functions to those provided by the electrodes of the epicardial lead(s). Alternatively, lead 108 may be a unipolar lead, and the pacing and/or sensing functions may be accomplished between a single electrode located on lead 108 and the epicardial electrode(s) or an electrode located on the housing of the IPG 100. However, lead 108 may also be one of the leads depicted in FIGS. 5 and 6 and described below or a conventional large surface area single polarity cardioversion/defibrillation electrode bearing lead for placement in the RA or CS.

It is not envisioned that the pacing level therapy provided as discussed above will always be successful to prevent all atrial fibrillation episodes in any single patient. Repeated attempts, however, can be undertaken without severe consequences. Unlike ventricular fibrillation, atrial fibrillation is not an immediately life threatening condition if prevention fails. If the invention is embodied in a system which also includes high voltage atrial defibrillation capabilities, the pacing level therapy of the present invention may be employed as an initial therapy to prevent atrial fibrillation, with the intended goal of simply reducing the number of atrial fibrillation or flutter episodes subject to atrial defibrillation. The large surface area electrodes 106R and 106L can in any case be used in the delivery of the cardioversion/defibrillation therapy.

FIG. 2 is a plan view of a lead 200 which may be substituted for the leads 106R and 106L of FIG. 1. A large surface area base pad 212 is provided supporting a plurality of spaced apart, discrete electrodes 210 which are electrically connected in common. A connector assembly 204 is provided at the proximal end of the lead 200 including a connector pin 206 for attachment to the IPG 100 as shown in FIG. 1. The plurality of discrete electrodes 210 are coupled electrically in common to connector pin 206 by means of an elongated insulated conductor inside lead body sheath 202. The plurality of electrodes 210 may be exposed areas of an underlying patch or coil electrode structure of the types described above that are insulated except where exposed.

Figure 3:
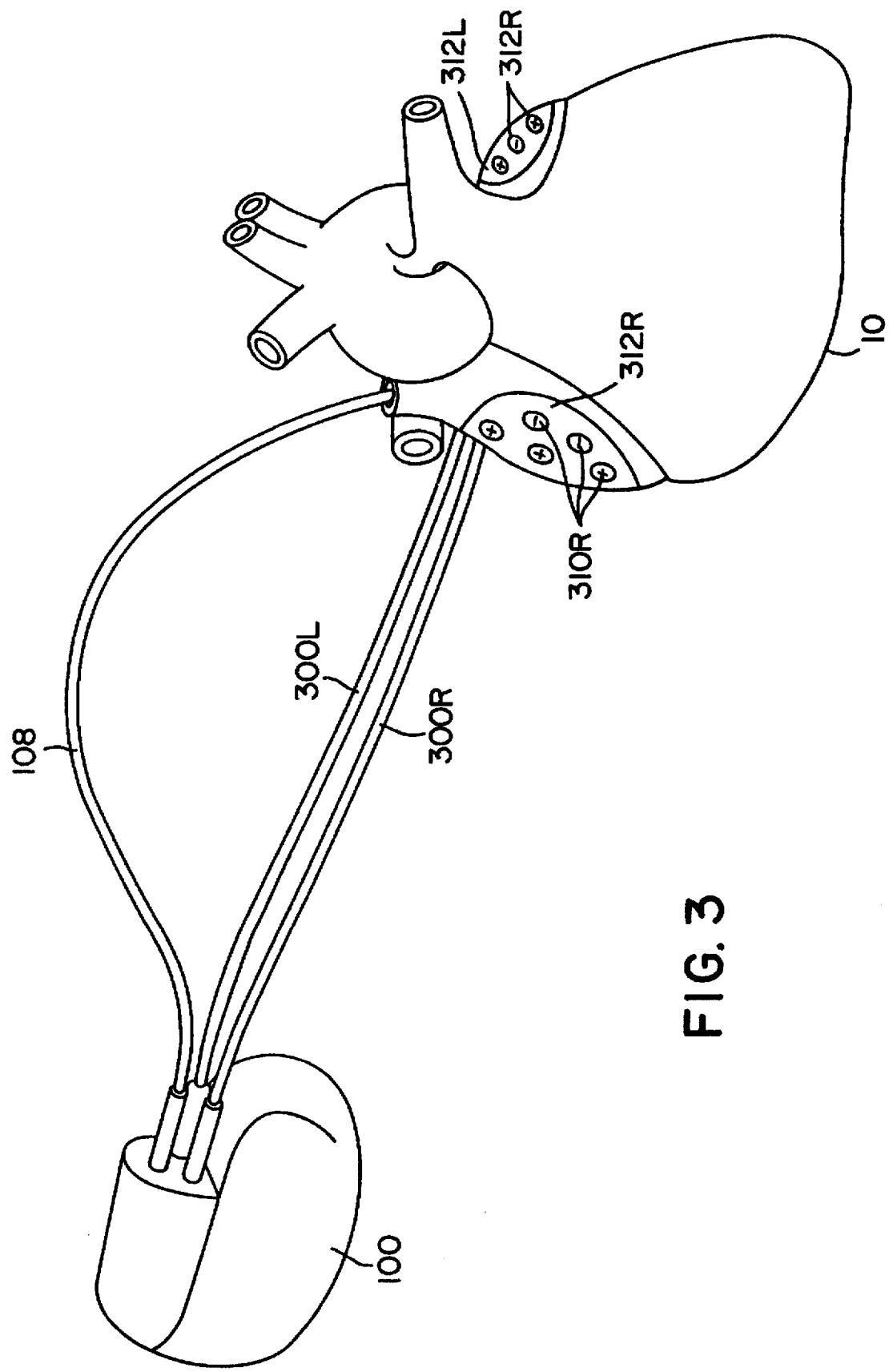
FIG. 3 is a plan view of a pacemaker IPG and a second associated lead system of the type in which the present invention may be embodied, illustrating the location of the leads and electrodes in relation to the atria of a human heart.

FIG. 3 is a plan view of a further pacing system in accordance with the present invention using an IPG 100 with an associated alternative atrial fibrillation prevention lead system, in conjunction with a human heart 10. As illustrated, the system optionally includes the right atrial lead 108 described above in reference to FIG. 1, and two epicardial electrode bearing leads 300R and 300L. Leads 300R and 300L are provided with a plurality of spaced apart electrode pairs 310R and 310L, respectively, located on flexible base pads 312R and 312L, respectively, adapted to be epicardially located on the right and left atria of the heart.

FIG. 4 is a plan view of a lead 300 which may be used as leads 300R, 300L illustrated in FIG. 3. The lead 300 includes multiple electrode pairs 310, located on silicone rubber electrode pad 312, each electrode pair 310 comprising a first, positive discrete electrode and a closely spaced, second, negative discrete electrode. All of the positive discrete electrodes are electrically connected in common and to a first conductor in lead body sheath 302 extending to a connector pin 308, for example. All of the negative discrete electrodes are similarly electrically connected in common and to a second conductor in lead body sheath 302 extending to a connector ring 304, for example. The positive and negative electrodes may be miniature conductive patches or turns of coiled conductor branches of the first and second conductors that are exposed in spots of the insulating pad 312. The number and arrangement of the electrode pairs 310 over the insulating pad 312 may be varied widely.

Figure 5:
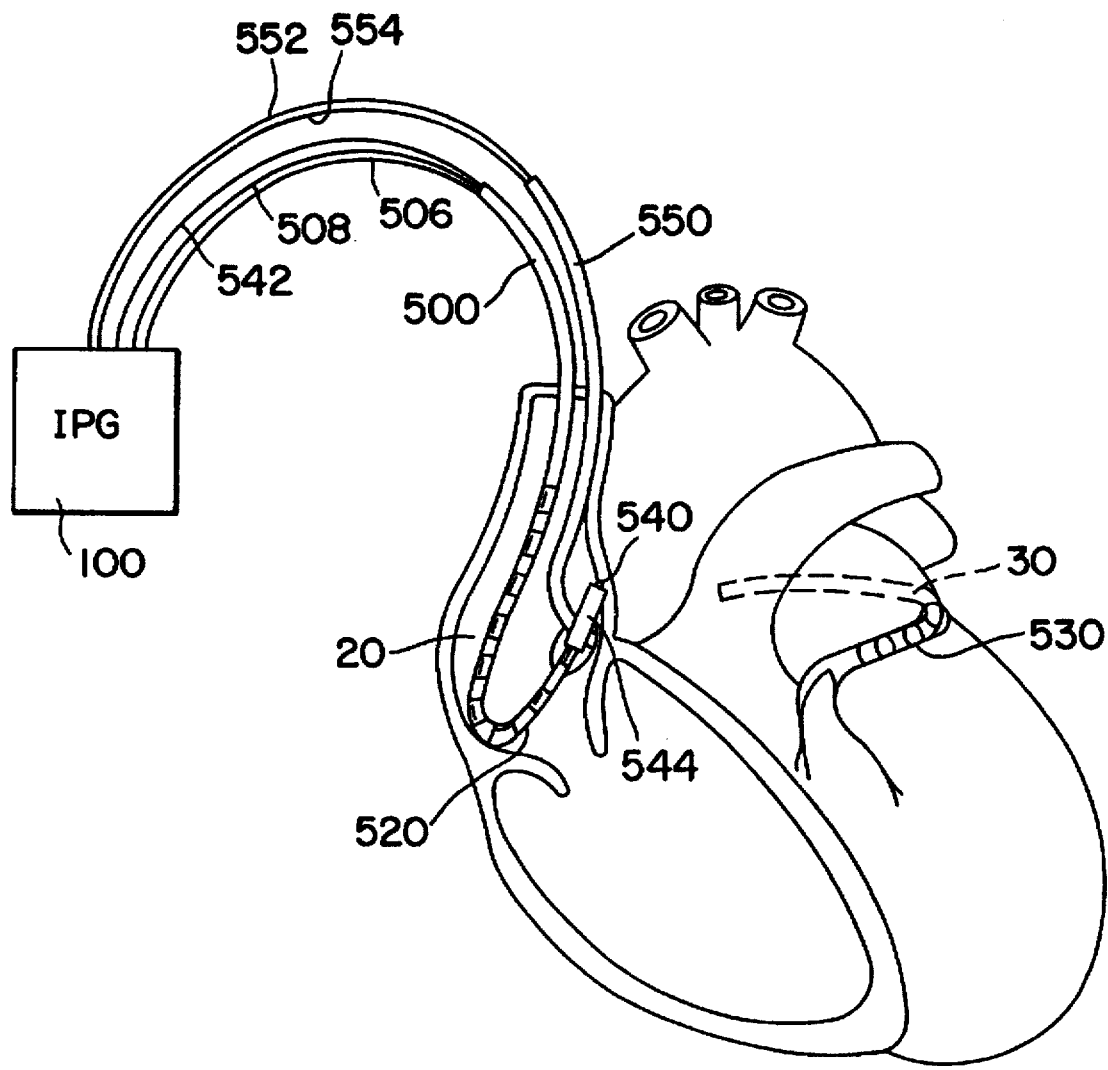
FIG. 5 is a plan view of a pacemaker IPG and a third associated lead system of the type in which the present invention may be embodied, illustrating the location of the leads and electrodes in relation to the atria of a human heart.

FIG. 5 is a further pacing system in accordance with the present invention using an IPG 100 with an associated second alternative atrial fibrillation prevention lead system in conjunction with a human heart 10 shown partially exposed. As illustrated, the lead system includes a RA endocardial lead 500 and a CS endocardial lead 550 placed in the right atrium 20 and in the coronary sinus 30 of the heart 10, respectively. The distal end section of the CS lead 550 including the is extended into the CS 30 and restrained there by the vein walls.

The RA endocardial lead 500 optionally includes the pace/sense electrode 540 adapted to be affixed in the right atrial appendage in a manner well known in the art and an associated conductor 542 functioning as one of the electrodes of the RA lead. The pace/sense electrode 540 may be a retractable helical electrode that can be extended from distal end housing 544 and screwed into the atrium for fixation and effective pacing and sensing in a manner well known in the art.

Leads 500 and 550 are each provided with elongated electrodes or electrode arrays 520 and 530, respectively. In embodiments similar to those of FIGS. 1 and 2, the electrodes 520 and 530 may be a single continuous electrode or spaced apart electrode arrays electrically connected in common. In a further embodiment as depicted in the lead of FIG. 6, a plurality of ring shaped (or other shaped) spaced apart electrodes 522 extend along distal sections of the leads 500, 550. In this embodiment, alternate electrodes 522 are electrically connected together and to positive and negative lead conductors, e.g. conductors 552 and 554 or 506 and 508, respectively, of the CS lead 550 and the RA lead 500, respectively, to form adjacent electrode pairs.

FIG. 6 may therefore be considered a plan view of the CS lead 550 and a variation on the RA lead 500' without an integral pace/sense electrode or electrode pair. The lead 550 includes multiple electrode pairs 510, located on insulated lead body 512, each electrode pair 510 comprising a first, positive discrete electrode and a closely spaced, second, negative discrete electrode. All of the positive discrete electrodes are electrically connected in common and to a first conductor in lead body 532 extending to a connector pin 536, for example, of lead connector 534. All of the negative discrete electrodes are similarly electrically connected in common and to a second conductor inside lead insulating sheath 532 extending to a connector ring 538, for example, of lead connector 534. The number and arrangement of the electrode pairs 510 along the insulating distal lead body 512 may be varied widely.

Figure 7:
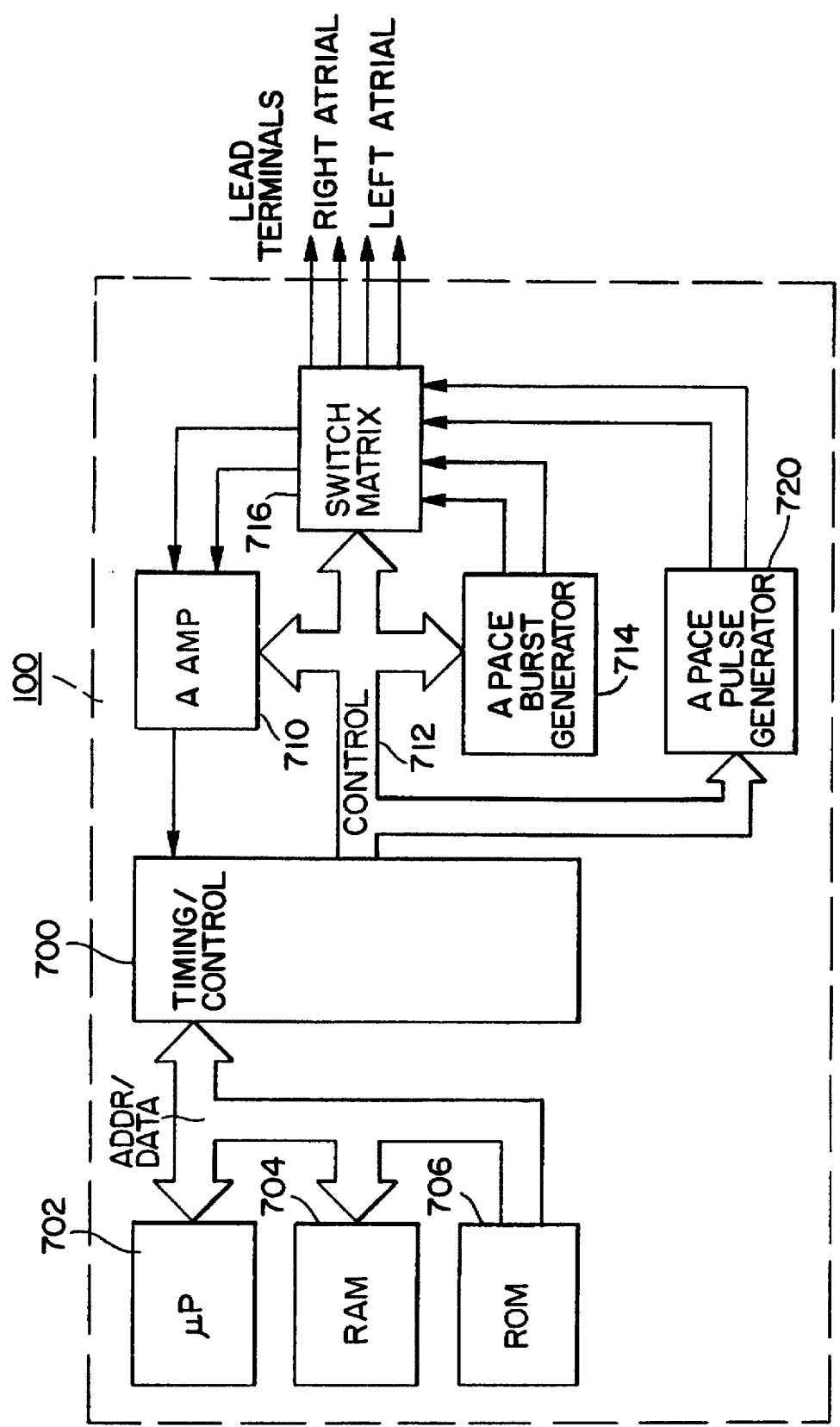
FIG. 7 is a block diagram of an implantable IPG having a switching matrix allowing sensing from multiple electrode pairs and delivery of simultaneous pacing pulse bursts to all electrode pairs of the electrode systems of FIGS. 1–6 in accordance with the various embodiments of the present invention.

FIG. 7 is a block diagram illustrating the major functional components of the implanted IPG 100, illustrated in FIGS. 1, 3 and 5 in the atrial burst pacing mode of the invention for preventing fibrillation and in the AAI pacing mode in response to atrial bradycardia with simultaneous delivery of the atrial pace pulse to all electrode pairs. All other possible pacing (and any other cardioversion or defibrillation) and sensing functions of the IPG 100 are not shown for simplicity.

The IPG 100 of FIG. 7 is provided with a switch matrix 716 for use with the single polarity epicardial or endocardial right and left atrial electrodes and associated leads described above or for use with the two polarity, electrode pair bearing, epicardial or endocardial leads in any combination and number of such leads. Switch matrix 716 shown in block format is simply a collection of FET and/or SCR switches activated under control of timing/control circuitry 700 to selectively couple the atrial burst pacing pulse generator 714 or the atrial pace pulse generator 720 or the atrial sense amplifier 710 to the lead system employed. The switch matrix 700 may be configured under control of the microprocessor 702 to make the connection with the lead conductors to the single pair of single polarity, large surface area electrode, or commonly connected discrete electrode, bearing leads. Or the switch matrix 716 may be configured to make the connection with the lead conductors to the electrode pairs of each of the two polarity, right and left atrial leads. Therefore, either only one or two connector pins or rings will be connected to the right atrial and left atrial lead terminals of the switch matrix 716 depending on the configuration and lead type used.

Atrial sense amplifier 710 can be any conventional cardiac sense amplifier circuits equivalent to any prior art atrial cardiac sensing circuits employed in previous devices as described in the above-referenced '578 application. Where the pace/sense electrodes are formed of closely spaced electrode pairs, as shown, for example, in FIGS. 3–6, sensing of near field atrial depolarizations may be effected across selected electrode pairs or across all of the electrode pairs on each lead. Multiple sense amplifiers may therefore be substituted for the single sense amplifier 710 depicted and coupled to each electrode pair or selected groups of electrode pairs. For example, a sense amplifier 710 may be provided and coupled to the electrode pairs for each of the RA endocardial or epicardial and LA epicardial or CS electrode bearing leads of the types depicted in FIGS. 3–6 used in any combination.

Timing and control functions for detecting an APB and delivering the pace pulse bursts in accordance with the invention are preferably accomplished using a microcomputer based system, corresponding to those used in presently available pacemakers. The basic function and operation of the timing and control logic circuitry 700, microprocessor 702, random access memory 704 and read only memory 706 may correspond to corresponding elements in the microcomputer controlled system disclosed in the above-referenced '578 application for an AAI pacing mode of operation.

The operation of microprocessor 702 is controlled by programming commands stored in read only memory 706 and in random access memory 704. The operation of the pulse generator 100 may be altered by the physician by altering the programming stored in memory 704, using control and telemetry circuitry conventional in implantable stimulators. Memory 704 may also be employed for storing measured parameters, such as P-P intervals, P-wave widths and amplitudes, the number, time and date of sensed APBs, number, time and date of delivery of burst therapies, etc. Memory 704 may also be employed to store digitized EGMs sensed during such events using the various electrodes provided. Microprocessor 702 also provides AAI pacing mode time intervals for atrial bradycardia pacing escape interval, refractory and blanking intervals, etc. conventionally employed in an AAI pacemaker. Communication to and from the microprocessor 702, memories 704 and 706 and control logic 700 is accomplished using address/data bus 708.

Timing/control circuitry 700, in conjunction with microprocessor 702, times out an atrial escape interval during which the atrial sense amplifier 710 is enabled to sense atrial depolarizations across the multiple sensing sites provided by the electrode system in use to provide an atrial sense event (ASE) in response to an atrial depolarization. In accordance with the present invention, a further atrial premature beat interval (APBI) is also started and timed out under the control of microprocessor 702 at each atrial sensed event (ASE) detected by atrial sense amplifier 710 or each atrial pace pulse (APACE) emitted by atrial pace output circuit 720. An atrial premature beat (APB) is detected when an ASE is detected during the time out of the APBI.

If no ASE is sensed during the APBI or the atrial escape interval, the atrial pace pulse generator 720 is enabled to deliver a pace energy pulse to all of the electrode pairs coupled to it through the switch matrix 716. Otherwise, an ASE resets the atrial escape interval. In this manner, AAI pacing in response to an atrial bradycardia is provided in a normal manner except that the pacing pulse is delivered simultaneously to all of the electrode pairs.

If the sense amplifier 710 detects the occurrence of an APB across any electrode pair coupled to atrial sense amplifier 710 via switch matrix 716, the timing and control circuit 700 provides the timing of the delivered atrial pace energy bursts by atrial pace burst generator 714 via control bus 712.

The low impedance atrial pacing output circuitry 720 may correspond generally to the output circuitry described in the above-referenced '578 application. The burst pulse circuit 714 is similarly constructed with the exception that it may be slightly modified to pace at higher voltages, (e.g. up to 10 or 15 volts) into somewhat lower impedances than typical implantable pacers, e.g., 50 ohms or less. This result may be accomplished by using a larger value output capacitor, for example in the range of 100 μF, and by increasing the voltage and current available for recharging the larger output capacitor. These modifications are believed to be well within the ability of one skilled in the art, and are therefore not discussed in detail. For purposes of the present invention any circuit capable of generating pacing pulses at an amplitude of 5 to 15 volts, with a pulse width of about 0.1 millisecond to about 5 milliseconds, should be sufficient. Other low energy pulses (i.e. 0.05 joules or less) having parameters outside these values may also be employed. The burst pulse amplitudes, widths, intervals and timing to the detected APB are all controlled by signals from the pacing/control block 700 received on control bus 712.

Figure 8:
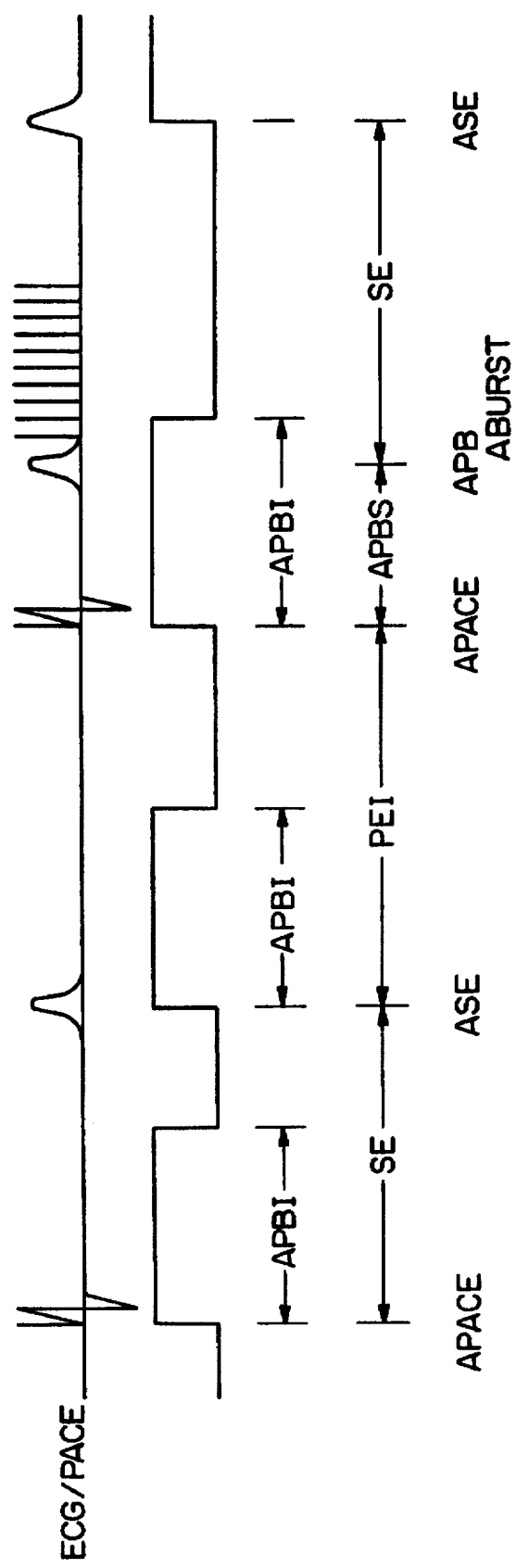
FIG. 8 is an illustration of a burst cycle of the IPG of FIG. 7 in response to a detected APB.

Turning to FIG. 8, a timing diagram of the detection of an APB and the simultaneous delivery of a burst of atrial pace pulses (ABURST) to all of the sites of the atrium contacted by the electrodes employed is depicted. After each APACE or ASE, the APBI and a pace escape interval (PEI) are timed. If no ASE occurs during the PEI, then an APACE is delivered to the pace sense lead 108 of FIGS. 1 and 3 or the pace/sense electrode 540 of RA lead 500, if present, or between all of the positive polarity and negative polarity atrial electrodes employed in the specific implementation.

For purposes of applying the pacing level ABURST fibrillation prevention therapy of the present invention, pacing pulses delivered at a frequency of 20–200 Hz are preferable. An extended series of pacing pulses (e.g. 10–100) may be delivered in a given burst. The pulse widths of the individual pulses are preferably in the range of 1.0 ms in width, and the amplitude may be on the order of 15.0 volts resulting in a delivered pulse burst energy on the order of 0.05 joules or less, if the burst includes at least 10 pulses. Preferably the burst is delivered for a time period sufficient to depolarize the entire atrium. For example, a burst of 100 milliseconds in duration may be delivered. The specific frequency, pulse amplitude, pulse width and number of pulses delivered in a burst may be selected by the implanting physician, following measurement of the rate of the patient's fibrillation. The burst rate may be, for example, slightly greater than the rate of the detected fibrillation. The intervals separating pulses in a pulse burst may be constant or variable, and may also be made programmable. As the delivered pulses are not specifically intended to be delivered synchronized to the atrial tissue adjacent the sensing electrodes where the APB was first detected, synchronization of the pacing pulses of the burst to the sensed APB is not necessary, and the pulse burst can be initiated at any convenient time following detection of an APB.

As a practical matter, because various portions of the atria will be in different stages of the depolarization-repolarization cycle, even if the first pulse in a pulse burst is delivered synchronized to the APB at one location, the delivered pulses will be asynchronous to depolarizations of other portions of the atria. For example, if large surface area electrodes are located one on each atrium, with sensing electrodes located in the right atrium, the delivered pacing pulse train will be generally asynchronous to depolarizations of the left atrium, regardless of the relationship of the pacing pulses to the sensed right atrial electrogram.

The pacemaker sense amplifier monitors the atrial electrogram to determine whether the pacing level pulses of a preceding burst were effective in terminating the sensed fibrillation. Alternatively or in addition, the IPG may monitor the atrial EGM to determine whether fibrillatory activity has ceased during delivery of the pulse train and terminate the delivery of the pulse train in response.

It will be understood that although leads and electrodes are depicted and described for delivering the pacing pulse bursts in relation to both the right and left atria, in practice, depending on the reentry pathways and other factors, only a single endocardial or epicardial lead bearing electrodes of the types described and depicted may be necessary in any given patient. In other words, only one such lead may be applied in relation to the right or left atria with a remote indifferent electrode used for such leads bearing single polarity electrodes as shown in FIGS. 1 and 2, for example.

Where large surface area, atrial electrode pairs of the types shown in FIGS. 1 and 2 are employed for simultaneously delivering the pacing pulse bursts to the atria, sensing across the atrial electrodes pair may optionally be augmented by sensing the ventricular electrogram through the use of a ventricular pace/sense electrode pair and ventricular sense amplifier and detection logic. The nearly simultaneous detection of an R-wave and a P-wave may be employed to classify the detected P-wave as a far field R-wave and to disregard it.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. A cardiac pacemaker, comprising:
   means for sensing atrial depolarizations of a patient' heart;
   means for defining atrial escape intervals following sensed atrial depolarizations;
   means for defining atrial premature beat sensing intervals less than the atrial escape intervals, following sensed atrial depolarizations;
   means for delivering atrial pacing pulses to the patient's heart in response to expirations of the atrial escape intervals in an absence of sensed atrial depolarizations during the atrial escape interval; and
   means for delivering atrial pacing pulses simultaneously to multiple points on a patient's atria in response to a single atrial depolarization sensed during a single atrial premature beat sensing interval.

2. A pacemaker according to claim 1 wherein the delivering means comprises means for delivering a burst of atrial pacing pulses simultaneously to multiple points on a patient's atria in response to a single atrial depolarization sensed during a single atrial premature beat sensing interval.

3. A pacemaker according to claim 1 or claim 2 wherein the delivering means comprises means for delivering atrial pacing pulses synchronized to a single atrial depolarization sensed during a single atrial premature beat sensing interval.

4. A pacemaker according to claim 1 or claim 2 wherein the delivering means comprises means for defining a delay interval following a single atrial depolarization sensed during a single atrial premature beat sensing interval means for delivering atrial pacing pulses on expiration of the delay interval.

5. A pacemaker according to claim 1 or claim 2 wherein the delivering means comprises means for inhibiting delivery of atrial pacing pulses in response to sensed atrial depolarizations occurring outside of atrial premature beat sensing intervals.

6. A pacemaker according to claim 5 wherein the delivering means comprises means for delivering atrial pacing pulses synchronized to a single atrial depolarization sensed during a single atrial premature beat sensing interval.

7. A pacemaker according to claim 5 wherein the delivering means comprises means for defining a delay interval following a single atrial depolarization sensed during a single atrial premature beat sensing interval means for delivering atrial pacing pulses on expiration of the delay interval.

8. A method of cardiac pacing, comprising:
   sensing atrial depolarizations of a patient's heart;
   defining atrial escape intervals following sensed atrial depolarizations;
   defining atrial premature beat sensing intervals less than the atrial escape intervals, following sensed atrial depolarizations;
   delivering atrial pacing pulses to the patients heart in response to expirations of the atrial escape intervals in an absence of sensed atrial depolarizations during the atrial escape intervals; and
   delivering atrial pacing pulses simultaneously to multiple points on a patient's atria in response to a single atrial depolarization sensed during a single atrial premature beat sensing interval.

9. A method according to claim 8 wherein the step of delivering atrial pacing pulses simultaneously to multiple points on a patient's atria in response to a sensed atrial depolarization comprises delivering a burst of atrial pacing pulses simultaneously to multiple points on the patient's atria.

10. A method according to claim 8 or claim 9 wherein the step of delivering atrial pacing pulses simultaneously to multiple points on a patient's atria in response to a sensed atrial depolarization during an atrial premature beat sensing interval comprises delivering the atrial pacing pulses synchronized to the sensed atrial depolarization.

11. A method according to claim 8 or claim 9 wherein the step of delivering atrial pacing pulses simultaneously to multiple points on a patient's atria in response to a sensed atrial depolarization during an atrial premature beat sensing interval comprises defining a delay interval following the sensed atrial depolarization and delivering the atrial pacing pulses on expiration of the delay interval.

12. A method according to claim 8 or claim 9, further comprising the step of inhibiting delivery of atrial pacing pulses in response to sensed atrial depolarizations occurring outside of atrial premature beat sensing intervals.

13. A method according to claim 12 wherein the step of delivering atrial pacing pulses simultaneously to multiple points on a patient's atria in response to a sensed atrial depolarization during an atrial premature beat sensing interval comprises delivering the atrial pacing pulses synchronized to the sensed atrial depolarization.

14. A method according to claim 12 wherein the step of delivering atrial pacing pulses simultaneously to multiple points on a patient's atria in response to a sensed atrial depolarization during an atrial premature beat sensing interval comprises defining a delay interval following the sensed atrial depolarization and delivering the atrial pacing pulses on expiration of the delay interval.

15. A method according to claims 8 or claim 9 wherein the step of delivering atrial pacing pulse on expirations of atrial escape intervals comprises delivering atrial pacing pulses simultaneously to multiple points on a patient's atria.

16. A method according to claim 15 wherein the step of delivering atrial pacing pulses simultaneously to multiple points on a patient's atria in response to a sensed atrial depolarization during an atrial premature beat sensing interval comprises delivering the atrial pacing pulses synchronized to the sensed atrial depolarization.

17. A method according to claim 15 wherein the step of delivering atrial pacing pulses simultaneously to multiple points on a patient's atria in response to a sensed atrial depolarization during an atrial premature beat sensing interval comprises defining a delay interval following the sensed atrial depolarization and delivering the atrial pacing pulses on expiration of the delay interval.

18. A cardiac pacemaker, comprising:
   means for sensing depolarizations of a patient's atria at a plurality of locations on the patient's atria;
   means for defining atrial escape intervals following sensed atrial depolarizations;
   means for defining atrial premature beat sensing intervals less than the atrial escape intervals, following sensed atrial depolarizations;
   means for delivering atrial pacing pulses to the patient's heart in response to expirations of the atrial escape intervals in an absence of atrial depolarizations sensed during the atrial escape interval; and
   means for delivering atrial pacing pulses simultaneously to the plurality of locations in response to a single atrial depolarization sensed at any of the plurality of locations during a single atrial premature beat sensing interval.

19. A pacemaker according to claim 18 wherein the delivering means comprises means for delivering a burst of atrial pacing pulses simultaneously to the plurality of locations in response to a single atrial depolarization sensed during a single atrial premature beat sensing interval.

20. A pacemaker according to claim 18 or claim 19 wherein the delivering means comprises means for delivering atrial pacing pulses synchronized to a single atrial depolarization sensed during a single atrial premature beat sensing interval.

21. A pacemaker according to claim 18 or claim 19 wherein the delivering means comprises means for defining a delay interval following a single atrial depolarization sensed during a single atrial premature beat sensing interval means for delivering atrial pacing pulses on expiration of the delay interval.

22. A pacemaker according to claim 18 or claim 19 wherein the delivering means comprises means for inhibiting delivery of atrial pacing pulses in response to sensed atrial depolarizations occurring outside of atrial premature beat sensing intervals.

23. A pacemaker according to claim 22 wherein the delivering means comprises means for delivering atrial pacing pulses synchronized to a single atrial depolarization sensed during a single atrial premature beat sensing interval.

24. A pacemaker according to claim 22 wherein the delivering means comprises means for defining a delay interval following a single atrial depolarization sensed during a single atrial premature beat sensing interval means for delivering atrial pacing pulses on expiration of the delay interval.

25. A method of cardiac pacing, comprising:
   sensing atrial depolarizations at a plurality of locations on a patient's atria;
   defining atrial escape intervals following sensed atrial depolarizations;
   defining atrial premature beat sensing intervals less than the atrial escape intervals, following sensed atrial depolarizations;
   delivering atrial pacing pulses to the patients heart in response to expirations of the atrial escape intervals in an absence of atrial depolarizations sensed during the atrial escape intervals; and
   delivering atrial pacing pulses simultaneously to the plurality of locations in response to a single atrial depolarization sensed at any of the plurality of locations during a single atrial premature beat sensing interval.

26. A method according to claim 25 wherein the step of delivering atrial pacing pulses simultaneously to the plurality of locations in response to a sensed atrial depolarization during an atrial premature beat sensing interval comprises delivering a burst of atrial pacing pulses simultaneously to the plurality of locations.

27. A method according to claim 25 or claim 26 wherein the step of delivering atrial pacing pulses simultaneously to the plurality of locations in response to a sensed atrial depolarization during an atrial premature beat sensing interval comprises delivering the atrial pacing pulses synchronized to the sensed atrial depolarization.

28. A method according to claim 25 or claim 26 wherein the step of delivering atrial pacing pulses simultaneously to the plurality of locations in response to a sensed atrial depolarization during an atrial premature beat sensing interval comprises defining a delay interval following the sensed atrial depolarization and delivering the atrial pacing pulses on expiration of the delay interval.

29. A method according to claim 25 or claim 26 wherein the step of delivering atrial pacing pulses simultaneously to the plurality of locations in response to a sensed atrial depolarization during an atrial premature beat sensing interval comprises inhibiting delivery of atrial pacing pulses in response to sensed atrial depolarizations occurring outside of atrial premature beat sensing intervals.

30. A method according to claim 29 wherein the step of delivering atrial pacing pulses simultaneously to the plurality of locations in response to a sensed atrial depolarization during an atrial premature beat interval comprises delivering the atrial pacing pulses synchronized to the sensed atrial depolarization.

31. A method according to claim 29 wherein the step of delivering atrial pacing pulses simultaneously to the plurality of locations in response to a sensed atrial depolarization during an atrial premature beat interval comprises defining a delay interval following the sensed atrial depolarization and delivering the atrial pacing pulses on expiration of the delay interval.

32. A method according to claim 25 or claim 26 wherein the step of delivering atrial pacing pulses on expirations of atrial escape intervals comprises delivering atrial pacing pulses simultaneously to the plurality of locations.

33. A method according to claim 32 wherein the step of delivering atrial pacing pulses simultaneously to the plurality of locations in response to a sensed atrial depolarization during an atrial premature beat interval comprises delivering the atrial pacing pulses synchronized to the sensed atrial depolarization.

34. A method according to claim 32 wherein the step of delivering atrial pacing pulses simultaneously to the plurality of locations in response to a sensed atrial depolarization during an atrial premature beat interval comprises defining a delay interval following the sensed atrial depolarization and delivering the atrial pacing pulses on expiration of the delay interval.

* * * * *